(12) United States Patent
Krullaards

(10) Patent No.: US 7,412,883 B2
(45) Date of Patent: Aug. 19, 2008

(54) TRAINING DEVICE

(76) Inventor: Robert Leonard Krullaards, Voorburgseweg 70, Leidschendam (NL) NL-2264 AH ( * ) Notice: Subject to any disclaimer, the term of this patent is extended or adjusted under 35 U.S.C. 154(b) by 517 days.

(21) Appl. No.: 11/106,544

(22) Filed: Apr. 15, 2005

(65) Prior Publication Data

US 2005/0250994 A1 Nov. 10, 2005

Related U.S. Application Data

(63) Continuation-in-part of application No. PCT/NL03/00697, filed on Oct. 15, 2003.

(30) Foreign Application Priority Data

Oct. 15, 2002 (NL) .................................... 1021653

(51) Int. Cl.
*A61B 5/22* (2006.01)
(52) U.S. Cl. ................................... 73/379.01
(58) Field of Classification Search .............. 73/379.01, 73/379.02, 379.03, 862.046, 862.41, 172; 128/782
See application file for complete search history.

(56) References Cited

U.S. PATENT DOCUMENTS

| | | | |
|---|---|---|---|
| 5,373,651 A * | 12/1994 | Wood | 36/114 |
| 5,429,140 A | 7/1995 | Burdea et al. | |
| 5,447,167 A * | 9/1995 | Fleischaker | 600/595 |
| 5,579,238 A | 11/1996 | Krugman | |
| 5,681,993 A * | 10/1997 | Heitman | 73/379.02 |
| 5,904,639 A | 5/1999 | Smyser et al. | |
| 2006/0007186 A1* | 1/2006 | Homer et al. | 345/179 |

FOREIGN PATENT DOCUMENTS

| | | |
|---|---|---|
| EP | 0 592 735 | 4/1994 |
| NL | 1 006 708 | 2/1999 |
| WO | WO 01/072223 | 10/2001 |

* cited by examiner

*Primary Examiner*—Jewel V Thompson
(74) *Attorney, Agent, or Firm*—Young & Thompson

(57) ABSTRACT

Device for detecting a pressure force exerted by a human muscle. If a sensor measures that a defined force is exceeded, a signal is emitted. This signal is used to indicate to the relevant person that he needs to modify his behavior. To determine the teaching effect of this signal, it is proposed for these signals to be stored in a memory and for the stored values to read out after a certain time and compared with more recent signals. The device can be used, inter alia, in a writing instrument which measures both the gripping force on the writing instrument and the writing pressure.

21 Claims, 1 Drawing Sheet toy, game, sporting item, or footwear

TRAINING DEVICE

BACKGROUND OF THE INVENTION

The present invention relates to a device for detecting a force exerted by a human muscle.

A device of this type is known from U.S. Pat. No. 5,429,140. This document describes a glove having sensors which generate signals which are transmitted to a computer. All the signals from the sensors are stored and processed in the computer.

DESCRIPTION OF THE RELATED ART

WO 0145561A1 (Tensor B.V./Smart Sense B.V.) describes a writing instrument provided with a squeezing force sensor. In the event of a defined squeezing force being exceeded, a signal is emitted. It has been found that the application of an excessive squeezing force impedes the circulation of blood in the shoulder area of the person who is writing, which can lead to complaints which can ultimately result in RSI-like symptoms.

It has been found that a pen of this type works particularly well and therefore positive results can be obtained particularly quickly. By adjusting the threshold value at which a signal is emitted, it is possible to gradually shift toward the desired state, certainly in the event of serious deviations.

However, in practice it has not proven easy to achieve such a state in targeted fashion.

SUMMARY OF THE INVENTION

The object of the present invention is to avoid this drawback and to provide a training device with which it is also possible to provide correction in the long term.

Moreover, it is an object of the present invention to provide a device which can be of compact structure and can be optimally controlled on the basis of a limited amount of data.

According to a first aspect the invention relates to a device for detecting a pressure force exerted by a human muscle in order to correct use of said muscle, which device comprises a force sensor and which device is provided with a memory, in which the signals originating from said force sensor are stored for at least a few days, as well as a readout/comparison device for reading out said stored signals after at least a week and/or comparing them with signals input more recently, said force sensor being designed to emit a warning signal in the event of a threshold value being exceeded, said warning signals being stored in said memory.

According to this aspect the signals emanating from the force sensor are stored in some way. During subsequent use, these signals are either read out and can then be compared with the current signals or are compared directly with the current signals. The effect and/or progress of improvement of the patient in question can be determined on the basis of this comparison, and any further measures required can be taken. Such measures may include, inter alia, altering the threshold value at which the force sensor becomes active in a specific way. According to the present invention, only those signals which exceed a defined threshold are stored. In this case, the exceeding of the threshold comprises at least the exceeding of a defined force, such as a squeezing force associated with a writing pressure of greater than 50-150 g. Moreover, according to a preferred embodiment, the threshold value can only be exceeded after a certain time delay, i.e. even if the above-mentioned absolute value is exceeded, recording only takes place after this force has been present for a prolonged period, such as for example a few seconds. The latter parameter is dependent on the particular use of the device. This results in more than just recording of the forces. After all, the present invention only records "undesirable" behavior, and action can be taken on the basis of such behavior. This can ultimately lead to improved behavior on the part of the user, which manifests itself in particular in a reduction in the deep neck muscle tension. In this way, it is possible to prevent RSI-like phenomena.

According to an advantageous embodiment, the force sensor is designed in such a manner that in the event of continuous application of a force which exceeds the threshold value, warning signals are emitted regularly.

According to an advantageous embodiment of the invention, the force sensor is incorporated in an implement. If this implement is relatively small, it may be expedient for the above-described memory and readout/comparison device to be arranged separately therefrom. For example, it is possible for the relevant signals to be stored, for example wirelessly, from an implement to a PC. Of course, it is also possible, in the case of relatively large objects, for at least the memory to be arranged therein.

With the present invention, it is possible to use a series of signals emitted during a single operation to ascertain information about the behavior of the user, i.e. it is possible to draw a distinction between brief and prolonged (incorrect) operation of an implement.

The force sensor described above may comprise a pressure sensor or a sensor for recording a squeezing force. This sensor may optionally be adjustable, both in terms of time and with regard to the force applied to it (threshold value). In addition to the pressure/squeezing forces being measured, they can also be displayed (optionally simultaneously).

A combination of this nature can be used, for example, in a writing instrument. In addition to the squeezing pressure, i.e. the force with which the writing instrument is held by the person writing, it is important to measure the pressure with which the writing instrument is pressed onto the paper or other substrate. A combination of the squeezing force and the pressure force has been found to give an accurate indication of whether or not the writer's behavior is as desired. Measurements have shown that the writing force is between 50 and 150 grams and is on average 70 grams. This pressure is slightly higher in the case of young people. By reducing the writing force, it is possible to obtain maximum relaxation in the neck-shoulder region. Moreover, it has been found that reducing the writing force more or less automatically causes the squeezing force to be reduced. The squeezing force can in principle be reduced to virtually zero, i.e. the writing instrument is scarcely held gripped by the fingers during writing. It has been found that holding the pen in a less cramped way and pressing the pen or other writing instrument less hard onto the writing surface causes more blood to circulate through the arm/shoulder/neck and moreover results in better coordination of finger control, i.e. writing. Also, reducing the cramped posture has a relaxing effect. Moreover, under certain circumstances it is possible to switch off the pressure force signal and to control/train only on the basis of squeezing force. In another variant, it is possible to signal a continuous low squeezing force using pressure pulses and thereby to draw conclusions as to the behavior of the writer. It is also possible for a pen to be of more or less intelligent design, i.e. for diagnosis, optionally in combination with an improvement schedule, to be made even during its first use.

As a result of these variables being stored and then compared, a period later, for example a few days, a week or longer later, with the squeezing/pressure force which is then current, it is possible to ascertain the progress of the writer. Threshold values for the various sensors can be adjusted on the basis of this progress. In addition to the variant in which threshold values can be set at the writing instrument (if appropriate using software), it is also possible to provide for a variant in which a number of different writing instruments are present, each having a different (fixed) threshold value. These different threshold values may encompass both the squeezing force and the pressure or writing force.

In the case of a sensor which comprises two partial sensors, such as the pressure sensor/sensor for recording a squeezing force described above, it is also possible to emit two different signals in the event of a defined threshold value being exceeded. These signals may comprise light, sound or vibration signals. If a threshold value of this type is exceeded repeatedly or for a prolonged period of time, it is possible to emit recurring signals. According to a particular variant of the present invention, this number of recurring signals is limited. For example, a value of approximately 50 may be mentioned. This makes it possible to prevent operation of a writing instrument or other instrument ending, for example as a result of batteries running out, if, for example, the instrument unintentionally enters a clamping position or other signal-emitting position.

As has already been indicated, the writing instrument can also be used to operate any keyboard-like structure, such as a keyboard, screen or the like (such as a calculator or electronic diary). In such a case, the tip of the writing instrument should be covered with an auxiliary structure. By using a specially designed cap, the user can select either to separate the writing instrument with writing tip as exposed part from the cap or to remove the writing instrument including the auxiliary piece from the cap.

The invention relates not only to the measurement of the pressure and squeezing force in a writing instrument, but rather numerous other applications in which problems may arise as a result of acquired deviations are also conceivable. Examples which may be mentioned, without constituting any form of limitation, include toothbrushes and other "tools" on which a squeezing force is exerted.

Musical instruments and in particular bows. Sporting equipment, such as tennis rackets. Chairs, backrests and/or arm rests thereof, beds, footwear and (medical) tools, such as a (dental) drill. Forces are also exerted on car steering wheels and handles of all kinds of objects. As a result of the device according to the invention being integrated in gloves, socks or other items of clothing, it is possible to accurately measure the behavior of the user and to provide advice on the basis of these measurements. In this context, it is important above all to record the forces at the point at which they engage with the surroundings.

A further important application is (pen) mice and/or joysticks which are known to cause RSI.

The threshold at which the first signal is emitted can be selected as a function of the particular application, and the time for which a threshold value has to be exceeded can also be set as a function of the particular application. This signal can also be modified for other purposes.

One example of the above is a car steering wheel. If a person steers using one hand or no hands for too long, an unsafe situation may arise, which is detected as an additional effect by the present device, so that a signal, optionally linked to further measures being taken, can be emitted.

In the case of the sporting equipment described above, consideration may be given in particular to tennis and golf. In these sports, undesirable situations may arise if an excessively high force is exerted on the equipment in question for a prolonged period of time. The present invention can be used to determine and correct a trend over the course of time.

Another possible application is beds, in which there is a risk of bedsores. Emitting a signal in good time makes it clear that the patient needs to adopt a different position. The device can also be used for babies, in order to check whether sufficient movement is present.

According to a further aspect the invention relates to a device for detecting a pressure force exerted by a human muscle in order to correct use of said muscle, which device comprises a force sensor and which device is provided with a memory, in which said force sensor is a sensor which records a squeezing force and is designed to emit a warning signal in the event of a threshold value being exceeded, said warning signals being stored in said memory. This embodiment is for example of importance with items which are gripped by hand such as a writing implement, a racket, a golf club and so on. It has been found that there is a relationship between squeeze force and writing pressure at a writing implement. Above a limit of 100-150 g pressure at writing undesirable effects in the human being result. This means that such pressure should be below 100-150 g and the related person should be trained to that end. The squeezing force should be correspondingly low. To that end the squeezing force (threshold) is preferably below 500 g and more in particular below 250 g such as below 200 g or 150 g. On the other hand the squeezing force (threshold) should be sufficient to engage the related item, i.e. above 25 g, more in particular above 50 g. According to a preferred embodiment of the invention optimum squeeze force is obtained being in the range of 75-125 g. It will be understood that this is the average squeeze force. For example, if a person uses a racket and hit the ball at that moment the squeeze force will have a considerable peak.

According to a further preferred embodiment of the invention only after exceeding a predetermined threshold as described above during a predetermined time a signal will be sent to the processing unit of the device. Generally, short pulses are not relevant in training a patient. Short is understood to be shorter than one second. The invention is most specifically directed to exceeding a threshold value during a longer time such as longer than several seconds. More in particular a value longer than 15 seconds is mentioned.

BRIEF DESCRIPTION OF THE DRAWINGS

The invention will be explained below with reference to a number of exemplary embodiments. In the drawing.

DESCRIPTION OF THE PREFERRED EMBODIMENT

Figure 1:
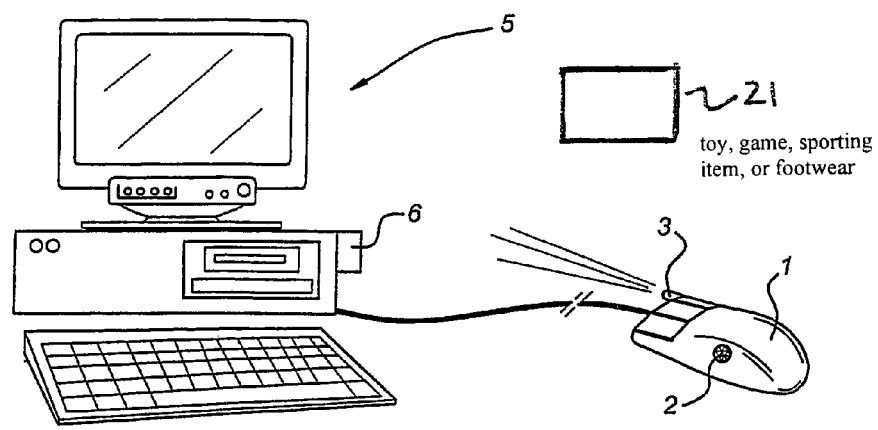
FIG. 1 diagrammatically depicts the use of the invention in a mouse.

In FIG. 1, a mouse is denoted by 1. Apart from the usual buttons, the mouse is also provided with a sensor 2. This sensor may also be arranged beneath the mouse as well as at the position indicated. Moreover, a transmitter denoted by 3 is also present. Additionally, the invention may be provided in a device such as a toy, game, a sporting item, and footwear, illustrated generically as block 21.

The PC operated by this mouse 1 is denoted overall by 5. However, it is provided with an additional processing unit 6, which is diagrammatically indicated and comprises a receiver for receiving the signal from transmitter 3.

This device operates as follows. When a user is working using the mouse and is exerting a high squeezing force on it, which is detected by sensor 2, a warning signal will be given on the screen after this threshold value has been exceeded for a certain time. This signal can be repeated regularly in the event of an excessively high gripping force continuing to be applied. A high squeezing force (threshold) is a squeezing force being more than 500 g particularly more than 200 g, 150 g, 100 g, 50 g respectively. More preferably the range of 75-125 g squeezing force should not be exceeded when engaging a writing implement. The time for exceeding such threshold value should be at least several seconds. If a higher squeezing force is used for only one second or less this is not detrimental.

Several thresholds might be present. A relatively high threshold might be set if this threshold is only exceeded for several seconds. A much lower threshold can be set for longer duration of an undesired condition. For example, if more than 15 seconds a relative lower undesired value is exceeded a further threshold might be overcome giving a signal to the processing unit.

Moreover, this signal is stored in the PC 5 and can be called up. This means that after a certain time, such as a few weeks, the user can see how he has modified his behavior with respect to the mouse. If the results are unfavorable, he needs to take measures to prevent the threshold value at which sensor 2 reacts from being exceeded.

Moreover, during the treatment over the course of time it is possible to reduce the threshold value at which a signal is emitted. This makes it possible to gradually shift from an unhealthy situation into a healthy situation. It has been found that in this way it is possible to eliminate RSI symptoms quickly and efficiently and permanent control is achieved after the correction has ended.

Figure 2:
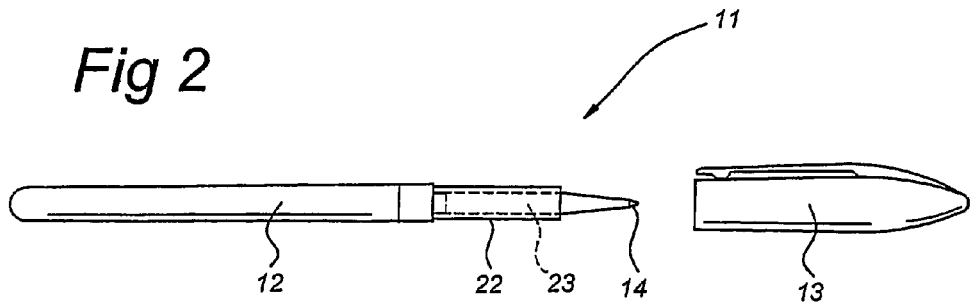
FIG. 2 shows a writing instrument according to the invention in a first position.

FIG. 2 diagrammatically depicts a writing instrument, which is denoted overall by 11. It comprises a standard sleeve 12 and a cap 13. 22 denotes the part in which the sensor for recording a squeezing force is arranged, for measuring the squeezing force exerted by the hand. Dashed lines indicate an insert part 23, which comprises a reservoir and a writing tip 14. According to an advantageous embodiment of the invention, this unit 23 can be exchanged, so that sleeve 12 and sensor part 22 can be used for both a ballpoint/roller pen, a fountain pen, a felt-tip pew, a pencil, etc. It is easy to introduce a different part 23. Signal lights (LEDs) which indicate that a threshold value has been exceeded, which are not shown, are incorporated in sleeve 12. As an alternative to lights, it is also possible to use a display, counter or the like.

Figure 3:
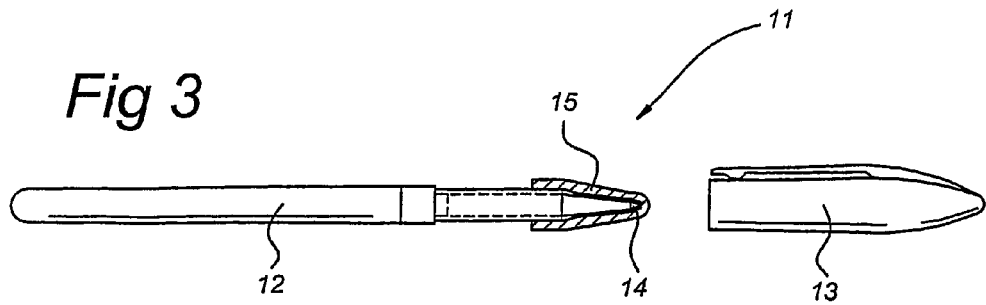
FIG. 3 shows the writing instrument shown in FIG. 2 in a second position.

FIG. 3 shows the same writing instrument 11 with an auxiliary cap 15 fitted over the writing tip 14.

Auxiliary cap 15 can easily be clipped on and may if appropriate be designed in different colors.

The design of this writing instrument is such that as a result of the cap 13 being actuated in a defined way, either writing tip 14 is released or auxiliary cap 15 is placed onto the front of the writing tip 14. In the position shown in FIG. 3, keyboard-like structures, such as pads, can be operated.

All this is important since the writing instrument 12 is provided, in a manner which is not shown in more detail, with both a sensor for measuring the squeezing force exerted by the fingers on the stem of a writing instrument 12 and with a pressure sensor, which records the force exerted on the free end of the pen when writing or when it is in contact with an operating panel. Moreover, part 12 incorporates signaling means which emit a signal as soon as a defined threshold value for either the pressure force or the squeezing force is exceeded. In this case too, recurring or alternating signals are emitted in the event of the undesired state continuing, and the threshold values can be adjusted downward. In this way, a distinction is drawn between brief peak forces and prolonged, undesirable tensioning of muscles.

The device described above can also be used for percussive instruments, such as tennis rackets and golf clubs. In such equipment, there is a high peak load which, however, only lasts for a short time. The introduction of a delay means that a short excessive force of this nature will not be recorded.

Although the invention has been described above on the basis of preferred embodiments, it will be understood that its range of applications is particularly broad. A specific design is associated with each application, and the precise embodiment of this design will be obvious after the above text has been read and lies within the scope of the appended claims.

The invention claimed is:

1. Device for detecting a pressure force exerted by a human muscle in order to correct use of said muscle, comprising:
    a force sensor that measures a pressure force exerted by a human muscle and provides signals indicating the measured force;
    a memory configured for storing i) the signals originating from said force sensor for at least plural days, ii) a threshold value, and iii) a warning signal indicating a recently measured pressure force exerted by the human muscle exceeds the threshold value and that the force exerted should be reduced; and
    a readout/comparison device for reading out said stored signals originating from said force sensor, said read-out stored signals having been stored in said memory at least a week and comparing the readout stored signals with signals from said force sensor input more recently than the week, said force sensor being designed to emit the warning signal in the event of the measured pressure force exceeding a threshold value, the warning signal indicating that the force exerted should be reduced.

2. Device as claimed in claim 1, in which said force sensor is designed in such a manner that in the event of continuous application of a force which exceeds the threshold value, warning signals are emitted regularly.

3. Device as claimed in claim 1, provided with means for processing a series of signals emitted successively.

4. Device as claimed in claim 1, in which the force sensor is incorporated in an implement and said memory and said readout/comparison device are arranged separately therefrom.

5. Device as claimed in claim 1, in which said force sensor is a pressure sensor and/or a sensor which records a squeezing force.

6. Device as claimed in claim 5, arranged in a writing instrument.

7. Device as claimed in claim 6, comprising sensors for recording the gripping force and writing pressure.

8. Device as claimed in claim 6, in which said writing instrument is provided with operating means for a PC.

9. Device as claimed in claim 1, arranged in footwear.

10. Device according to claim 1, arranged in a toy, game or item of sporting equipment.

11. Device as claimed in claim 1, comprising a loadability measurement, wherein the force detected by the force sensor over the course of time is recorded.

12. Device as claimed in claim 1, in which said force sensor is designed to emit a warning signal only after the threshold value has been exceeded for a defined time.

13. Device for detecting a pressure force exerted by a human muscle in order to correct use of said muscle, which device comprises a force sensor and which device is provided with a memory, in which said force sensor is a sensor which records a squeezing force and is designed to emit a warning signal in the event of a threshold value being exceeded, said warning signals being stored in said memory.

14. Device according to claim 13, wherein said threshold is below 500 g.

15. Device as claimed in claim 1, wherein only signals exceeding a defined threshold value are stored in the memory.

16. Device according to claim 15, wherein the defined threshold value is a writing pressure.

17. Device as claimed in claim 13, in which the force sensor is incorporated in an implement and said memory and said readout/comparison device are arranged separately therefrom.

18. Device as claimed in claim 13, comprising sensors for recording the gripping force and writing pressure.

19. Device as claimed in claim 18, in which said writing instrument is provided with operating means for a PC.

20. Device according to claim 13, arranged in a toy, game or item of sporting equipment.

21. Device as claimed in claim 13, comprising a loadability measurement, wherein the force detected by the force sensor over the course of time is recorded.

* * * * *